United States Patent
Ehlert

(10) Patent No.: US 11,644,026 B2
(45) Date of Patent: May 9, 2023

(54) DEVICE FOR SUCTIONING BODILY FLUIDS AND FOR SUPPLYING A SUBSTANCE

(71) Applicant: MEDELA HOLDING AG, Baar (CH)

(72) Inventor: Hilmar Ehlert, Hergiswil (CH)

(73) Assignee: MEDELA HOLDING AG, Baar (CH)

( * ) Notice: Subject to any disclaimer, the term of this patent is extended or adjusted under 35 U.S.C. 154(b) by 240 days.

(21) Appl. No.: 16/333,877

(22) PCT Filed: Sep. 18, 2017

(86) PCT No.: PCT/EP2017/073466
§ 371 (c)(1),
(2) Date: Mar. 15, 2019

(87) PCT Pub. No.: WO2018/054834
PCT Pub. Date: Mar. 29, 2018

(65) Prior Publication Data
US 2019/0201598 A1    Jul. 4, 2019

(30) Foreign Application Priority Data

Sep. 20, 2016    (EP) ..................... 16189671

(51) Int. Cl.
*F04B 43/02* (2006.01)
*A61M 1/00* (2006.01)
(Continued)

(52) U.S. Cl.
CPC .......... *F04B 43/02* (2013.01); *A61F 9/00736* (2013.01); *A61M 1/77* (2021.05);
(Continued)

(58) Field of Classification Search
CPC .......... A61M 2205/12; A61M 2202/08; A61M 2209/086; A61M 5/14232; A61M 1/77;
(Continued)

(56) References Cited

U.S. PATENT DOCUMENTS

| 4,634,024 | A | | 1/1987 | Vollenweider |
| 5,125,891 | A | * | 6/1992 | Hossain ............... F04B 43/1253 417/477.2 |

(Continued)

FOREIGN PATENT DOCUMENTS

| CN | 104771801 A | 7/2015 |
| DE | 202015006341 U1 | 11/2015 |

(Continued)

OTHER PUBLICATIONS

U.S. Appl. No. 16/335,143, filed Mar. 20, 2019 (as US national phase of PCT/EP2017/073464, international filing date Sep. 18, 2017).

(Continued)

*Primary Examiner* — Erich G Herbermann
*Assistant Examiner* — Seth Han
(74) *Attorney, Agent, or Firm* — Marshall, Gerstein & Borun LLP

(57) ABSTRACT

A device for aspirating body fluids and for supplying a substance to a human or animal body is defined. The device comprises a first pump (8) for the aspiration of the body fluids, and a second pump (3), or a coupling element (76') for connecting a second pump (3') in order to convey the substance to the body by means of the second pump (3, 3'). Moreover, the device comprises a drive (70, 70') for driving the first pump (8). The same drive (70, 70') which serves to drive the first pump (8) also serves to drive the second pump (3, 3').

13 Claims, 4 Drawing Sheets

(51) Int. Cl.
*A61F 9/007* (2006.01)
*F04B 43/12* (2006.01)
*F04B 43/14* (2006.01)
*A61M 25/00* (2006.01)

(52) U.S. Cl.
CPC .............. *A61M 1/772* (2021.05); *A61M 1/80* (2021.05); *A61M 1/90* (2021.05); *F04B 43/1253* (2013.01); *F04B 43/14* (2013.01); *A61B 2217/005* (2013.01); *A61B 2217/007* (2013.01); *A61M 25/00* (2013.01); *A61M 2202/08* (2013.01)

(58) Field of Classification Search
CPC .......... A61M 1/74; A61M 1/772; A61M 1/80; A61M 1/802; A61M 1/90; A61M 1/92; A61M 1/91; A61M 1/0058; A61M 1/0088; A61M 1/0072; A61B 2217/005; A61B 2217/007; F04B 43/025; F04B 23/08; F04B 23/04; F04B 43/02; F04B 43/1253; A61F 9/00736
USPC ........................................................ 604/315
See application file for complete search history.

(56) References Cited

U.S. PATENT DOCUMENTS

| | | | | |
|---|---|---|---|---|
| 5,388,972 | A * | 2/1995 | Calhoun | F04B 43/1253 417/477.11 |
| 5,611,335 | A * | 3/1997 | Makhoul | A61M 16/161 128/205.15 |
| 5,772,255 | A * | 6/1998 | Osborne | A61M 39/12 285/179 |
| 6,280,440 | B1 * | 8/2001 | Gocho | A61B 18/1492 604/151 |
| 6,290,690 | B1 * | 9/2001 | Huculak | A61M 1/0058 604/521 |
| 6,454,543 | B1 * | 9/2002 | Beck | B60T 8/4022 417/199.1 |
| 8,591,453 | B2 | 11/2013 | Stubkjaer et al. | |
| 9,421,322 | B2 * | 8/2016 | Breitweiser | A61M 5/16804 |
| 2004/0073177 | A1 * | 4/2004 | Hickle | A61M 5/172 604/257 |
| 2004/0202561 | A1 | 10/2004 | Hershberger et al. | |
| 2006/0025727 | A1 * | 2/2006 | Boehringer | A61M 1/0088 604/313 |
| 2006/0073048 | A1 * | 4/2006 | Malackowski | A61M 3/0258 417/474 |
| 2007/0128046 | A1 * | 6/2007 | Gonnella | F04B 43/088 417/2 |
| 2007/0258838 | A1 * | 11/2007 | Drake | F04B 43/0072 417/477.2 |
| 2008/0132763 | A1 * | 6/2008 | Isaacson | A61B 1/313 600/158 |
| 2008/0147008 | A1 * | 6/2008 | Lewis | A61M 5/172 604/155 |
| 2008/0154182 | A1 | 6/2008 | Martin et al. | |
| 2008/0154184 | A1 | 6/2008 | Blight et al. | |
| 2008/0154185 | A1 | 6/2008 | Blight | |
| 2010/0036333 | A1 * | 2/2010 | Schenk, III | A61M 1/734 604/313 |
| 2013/0085462 | A1 * | 4/2013 | Nip | A61M 1/0058 604/315 |
| 2013/0150782 | A1 * | 6/2013 | Sorensen | A61F 9/00745 604/319 |
| 2014/0163487 | A1 | 6/2014 | Tout et al. | |
| 2016/0015873 | A1 | 1/2016 | Robinson et al. | |
| 2016/0095964 | A1 | 4/2016 | Tapadiya | |

FOREIGN PATENT DOCUMENTS

| | | |
|---|---|---|
| EP | 0293081 A1 | 11/1988 |
| EP | 2883555 A2 | 6/2015 |
| FR | 2624376 A1 | 6/1989 |
| FR | 2624377 A1 | 6/1989 |
| FR | 2624378 A1 | 6/1989 |
| FR | 2960423 A1 | 12/2011 |
| WO | WO-98/06446 A2 | 2/1998 |
| WO | WO-2011/018132 A1 | 2/2011 |
| WO | WO-2014/045047 A1 | 3/2014 |
| WO | WO-2015091070 A1 | 6/2015 |
| WO | WO-2016/065335 A1 | 4/2016 |
| WO | WO-2016054470 A1 | 4/2016 |

OTHER PUBLICATIONS

International Search Report for International Application No. PCT/EP2017/073464, dated Apr. 9, 2018.

International Search Report for International Application No. PCT/EP2017/073466, dated Feb. 28, 2018.

European Communication for Application No. 17769056.7, dated Nov. 21, 2022.

* cited by examiner

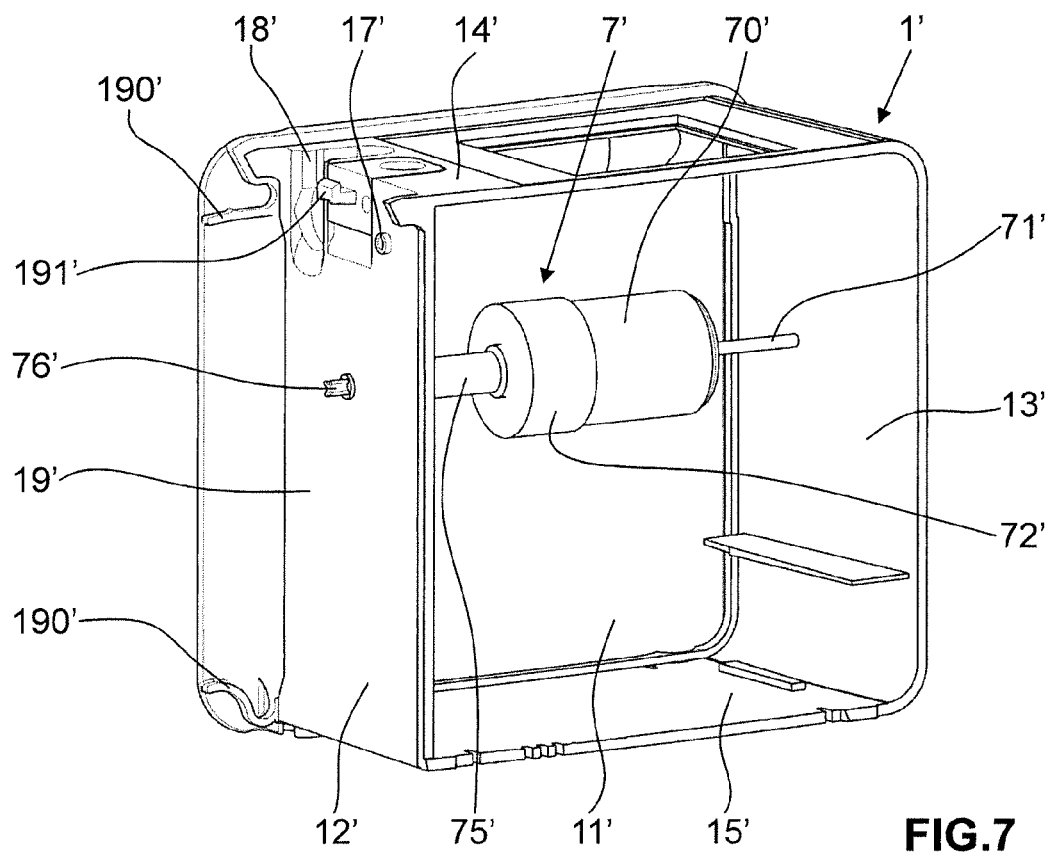
FIG. 7
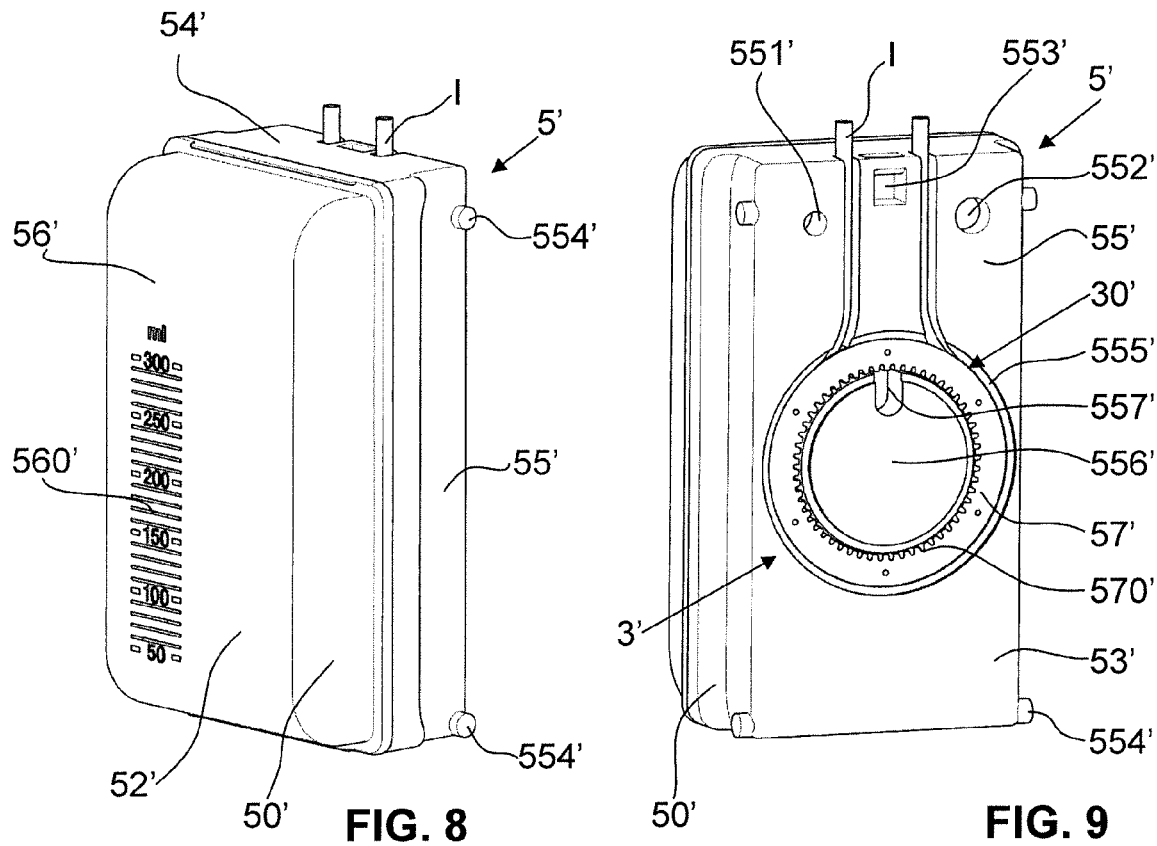
FIG. 8
FIG. 9

DEVICE FOR SUCTIONING BODILY FLUIDS AND FOR SUPPLYING A SUBSTANCE

CROSS-REFERENCE TO RELATED APPLICATION

The present application is the US national phase of International Application No. PCT/EP2017/073466, filed Sep. 18, 2017, which claims priority to European Application No. 16189671.7, filed Sep. 20, 2016. The priority application, EP 16189671.7, is hereby incorporated by reference in its entirety.

TECHNICAL FIELD

In order to achieve this object the present invention relates to a device for aspirating body fluids and for supplying a substance to a human or animal body. Devices of this type are used, in particular, in the medical field, for instance in negative pressure wound therapy combined with instillation or irrigation, in eye surgery or in fat removal.

PRIOR ART

In the medical field there are various applications in which, on the one hand, body fluids or secretions from body cavities or wounds are aspirated by means of a pump and, on the other hand, a substance is supplied to the body. Possible fields of application concern, in particular, negative pressure wound therapy combined with instillation, eye surgery and liposuction (fat removal). Depending on the application, the aspiration and the supplying here take place simultaneously, one after the other and/or intermittently in alternation.

The substance to be supplied can be, for instance, a physiological or non-physiological saline solution, a drug or a mixture thereof. The substance can serve, for example, to promote wound healing, to prevent infections or for local anaesthesia. The supplying of the substance can thus be used for flushing or for therapeutic, diagnostic and/or preventive purposes.

For the supplying of the substance, in much the same way as in conventional infusion, a liquid-containing pouch filled with the substance to be supplied, or a bottle, is often disposed in elevated position over the body site to be treated, so that the substance, owing to the hydrostatic pressure, is supplied through a supply line to the site to be treated. Separately thereto, the body fluids are aspirated by a vacuum pump via an appropriate line.

In order to enable better adjustment and regulation in the supplying of the substance, and/or to be independent of the arrangement and, in particular, the vertical position of the liquid container filled with the substance, systems in which the supplying of the substance to the body is realized by means of a pump, in particular a so-called peristaltic or flexible-tube pump, are also well known.

For instance, WO 2016/054470 shows a device of this type, having a first pump for supplying substances to a wound region and having a second pump for aspirating fluids from the wound region.

The operation of such devices is often laborious for the user, since, on the one hand, the pump for the supplying of the substances and, on the other hand, the pump for the aspiration, must be correctly installed and adjusted.

In order to reduce the complexity of equipment involved in the treatment, apparatuses are known in which the pump for aspirating the body fluids and the pump for supplying of the substance are housed in a common housing.

For instance, WO 2015/091070, along with US 2008/0154184, US 2008/0154182, U.S. Pat. No. 8,591,453 and US 2008/0154185, discloses an apparatus having two pumps disposed in a common housing, of which one serves for the aspiration of body fluids and the other serves for the supplying of a substance.

In US 2014/0163487 too, such an apparatus having two pumps is disclosed, wherein the pump head of a peristaltic pump, which serves to supply a substance to the body, is disposed on the outer side of the pump unit housing. A liquid container, which serves to receive an instillation liquid, can be connected up to the pump unit housing. On the liquid container is configured a tube guide, by virtue of which the pump head, if the container is connected up to the pump unit housing, applies an appropriate pumping action to the instillation tube leading out of the inside of the container, in order thus to pump the instillation liquid towards the body.

These devices, which serve, on the one hand, for the aspiration of body fluids and, on the other hand, for the supplying of a substance, mostly have a considerable volume and weight. Moreover, they are complex and correspondingly costly in terms of production.

Further devices of the generic type are disclosed, for example, in EP 2 883 555, CN 104771801, U.S. Pat. No. 4,634,024.

SUMMARY OF THE INVENTION

It is therefore an object of the invention to create a versatile device for aspirating body fluids and for supplying a substance to a human or animal body, which device has a low volume and weight. Moreover, the device should be easily operable for the user.

In order to achieve this object, the present invention provides a device for aspirating body fluids and for supplying a substance to a human or animal body, comprising
 a first pump for the aspiration of the body fluids;
 a second pump, or a coupling element for connecting a second pump in order to convey the substance to the body by means of the second pump; and
 a drive for driving the first pump.
The same drive which serves to drive the first pump here also serves to drive the second pump.

As the same drive is used to drive both pumps, the device can be dimensioned smaller in total and, moreover, can have a smaller weight. The device can thereby be configured, in particular, such that it is portable, that is to say that it can be comfortably carried by a user alone and without excessive effort. Advantageously, the device further has a compact construction overall. Owing to the just one drive, the device is less prone to faults and can be produced more cheaply overall.

The first pump is preferably a vacuum pump, in particular a diaphragm pump. A diaphragm pump generally has at least one diaphragm and a pumping chamber limited by this same. The device can additionally comprise a valve, in particular a pneumatic valve, by means of which the vacuum pump is connectable to the environment in order at least partially, or even fully, to aspirate air from the environment instead of body fluids. The valve can in particular be connected to a vacuum port of the vacuum pump, to which vacuum port a suction line is connectable. By switchover of the valve, the vacuum port can, where necessary, be at least partially or even fully connected to the environment instead of to the suction line. The valve enables the suction power for the aspiration of the body fluids to be varied, whilst the motor power remains constant.

The second pump is preferably a peristaltic pump. Peristaltic pumps are also known by the term flexible-tube pumps and are particularly suitable for a pulsating supplying of a substance, in particular of a fluid substance such as a liquid, to the body. A peristaltic pump generally has at least one rotatably mounted pump head, to which, for example, pressure rollers or sliding shoes are attached.

The device according to the invention is used for medical purposes, in particular for the negative pressure treatment, combined with instillation or irrigation, of wounds on the human or animal body. Other fields of application are possible, however, for instance the combined fat removal and flushing in liposuction or the flushing of catheters for the avoidance of blockages, or the combined aspiration and flushing in eye surgery.

In one specific embodiment, the device has a coupling element for the connection of the second pump. The second pump is in this case not part of the device, but rather can be coupled to the device via the coupling element in such a way that it can be driven by the drive. The second pump can here be designed, in particular, only for single use, so as afterwards to be exchanged and disposed of. The thereby resulting lower requirements regarding the life of the pump enable a particularly favourable production of the second pump, which can advantageously be made, even substantially fully, from injection moulded parts.

The device preferably has a fluid-collecting container for collecting the aspirated body fluids. For reasons of hygiene, the fluid-collecting container is often designed for single use. In particular where the second pump is also designed for single use, it can be integrated in the fluid-collecting container, so that fluid-collecting container can be coupled with the second pump to the coupling element.

The device preferably has at least a first freewheel, by means of which the first pump or the second pump or the coupling element is coupled to the drive. The freewheel can in particular produce the effect that, depending on the rotational direction of the drive, either both pumps are driven in tandem, or that only the first pump or only the second pump is driven. This can be desirable for certain applications.

The first freewheel can couple, for example, the first pump to the drive. Preferably, a second freewheel is then present, by means of which the second pump or the coupling element is coupled to the drive. The second freewheel advantageously has an opposite freewheel direction in comparison to the first freewheel. It can thereby in particular be ensured that, depending on the rotational direction of the drive, either the first pump or the second pump is driven, but not both together. That is to say, either a substance is supplied to the body, or body fluids are aspirated, but not both at the same time.

The first and, if present, second freewheel can be constituted, for instance, by a sprag clutch, by a wrap spring clutch (spring-winding freewheel), or by a self-synchronizing clutch.

The drive is generally constituted by a motor, in particular by an electric motor. In an in particular preferred embodiment, this is in form of a brushless direct-current motor, since such a motor can generally be operated at low speeds of less than 100 r.p.m. Moreover, a brushless direct-current motor allows a relatively low-amplitude pressure regulation, whereby a very accurate control of the pressure (underpressure or overpressure) becomes possible.

The device advantageously has a pump unit housing having an interior in which at least the first pump and the drive are housed. The second pump can likewise be disposed in the interior of the pump unit housing. Preferably, however, either the second pump is disposed on an outer side of the pump unit housing, or a coupling element for connecting a second pump to the device is disposed on an outer side of the pump unit housing.

A simple embodiment is obtained, in particular, when the device has a drive train in which the drive is disposed between the first pump and the second pump or the coupling element.

In order to enable a particularly high versatility of the device, this is advantageously configured such that the pumping power of the first pump, on the one hand, and the pumping power of the second pump or the power produced by the coupling element, on the other hand, are adjustable independently of each other. The adjustability here relates less to the production, than to the use of the finished device. The independent adjustability of the pumping power of the first and the second pump can be achieved in a variety of ways. Thus this can be achieved, for example, by means of one or more freewheels in combination with a valve connected up to a vacuum pump. The use of gear mechanisms in combination with, for example, a freewheel is possible. Further options are conceivable.

In certain embodiments, a drive train having at least one gear mechanism can thus be provided, by means of which the drive is coupled to the first pump or to the second pump or to the coupling element. Owing to the gear mechanism, the first or second pump can be driven at a speed different from the drive.

In one specific embodiment, a container holding the substance to be supplied is attachable to the device. The container can have an identification feature and the device an identification unit, in order to identify what type of substance is contained in the container. The device can then in particular be configured to select or preselect, in dependence on the identified type of substance, one of several possible operating modes for driving the first pump and the second pump or the coupling element.

BRIEF DESCRIPTION OF THE DRAWINGS

Preferred embodiments of the invention are described below with reference to the drawings, which serve merely for illustration and should not be interpreted restrictively. In the drawings:

FIG. 7 shows a perspective view of a schematically shown device according to a third embodiment according to the invention, wherein the front wall of the pump unit housing is omitted;

FIG. 8 shows a first perspective view of a fluid-collecting container, which is suitable for connecting up to the device of FIG. 7; and FIG. 9 shows a second perspective view of the fluid-collecting container of FIG. 8.

DESCRIPTION OF PREFERRED
EMBODIMENTS

Figure 3:
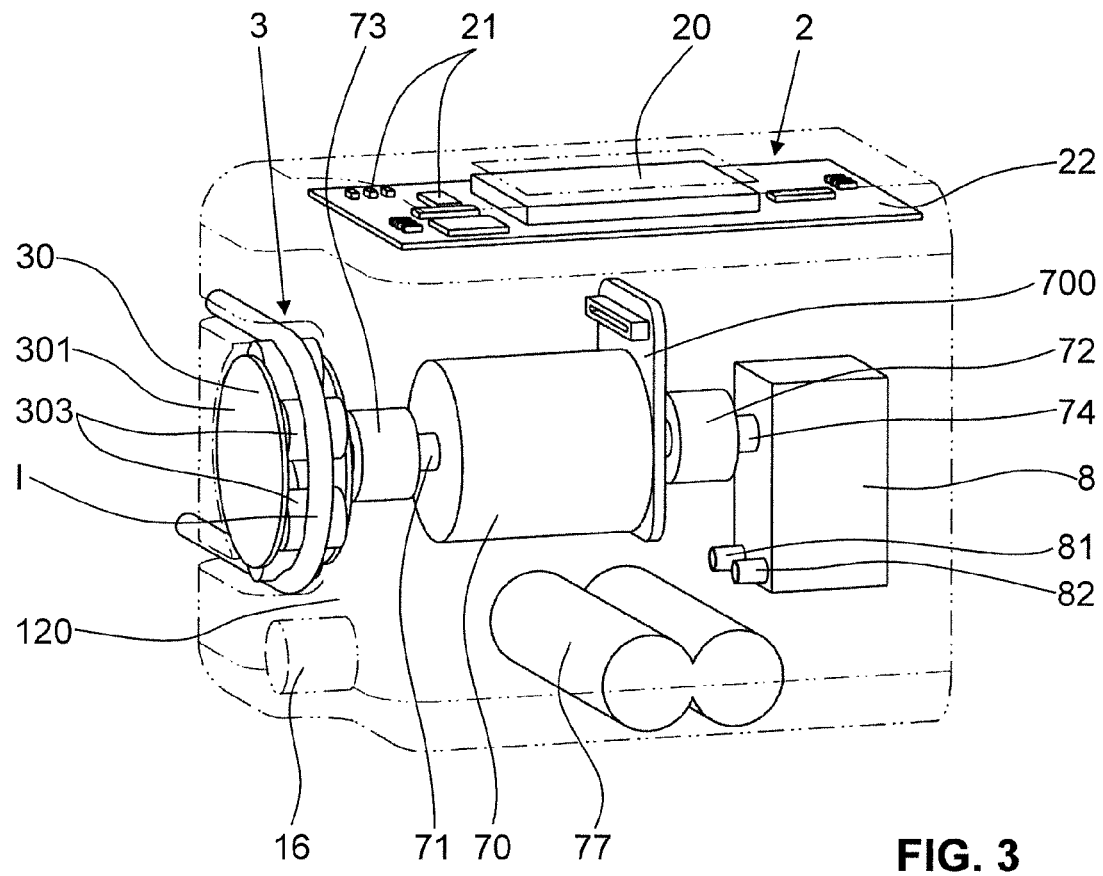
FIG. 3 shows a perspective view of the device of FIG. 1, wherein the pump unit housing is indicated only with dashed lines.
Figure 4:
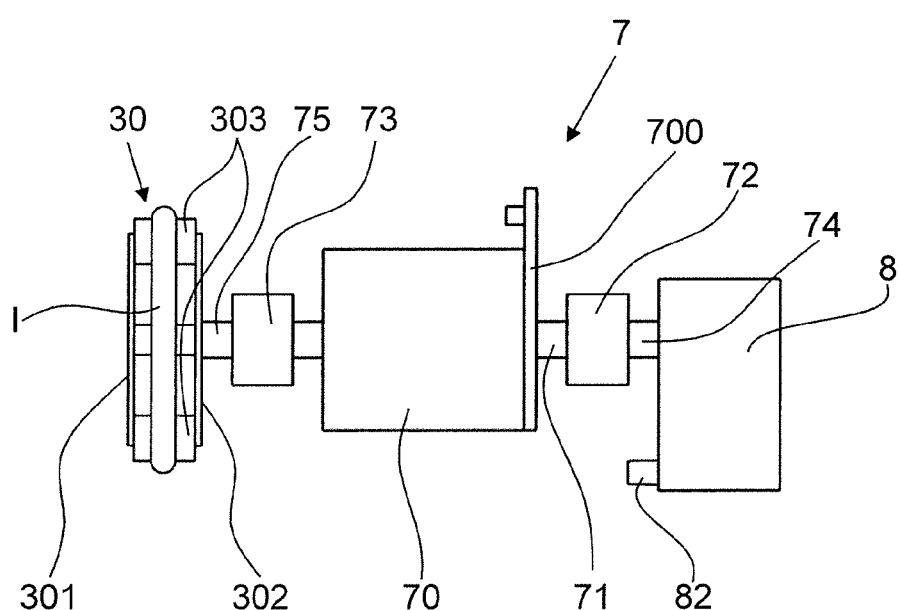
FIG. 4 shows a top view of the drive train, the pump head of the peristaltic pump and the diaphragm pump of the device of FIG. 1.
Figure 5:
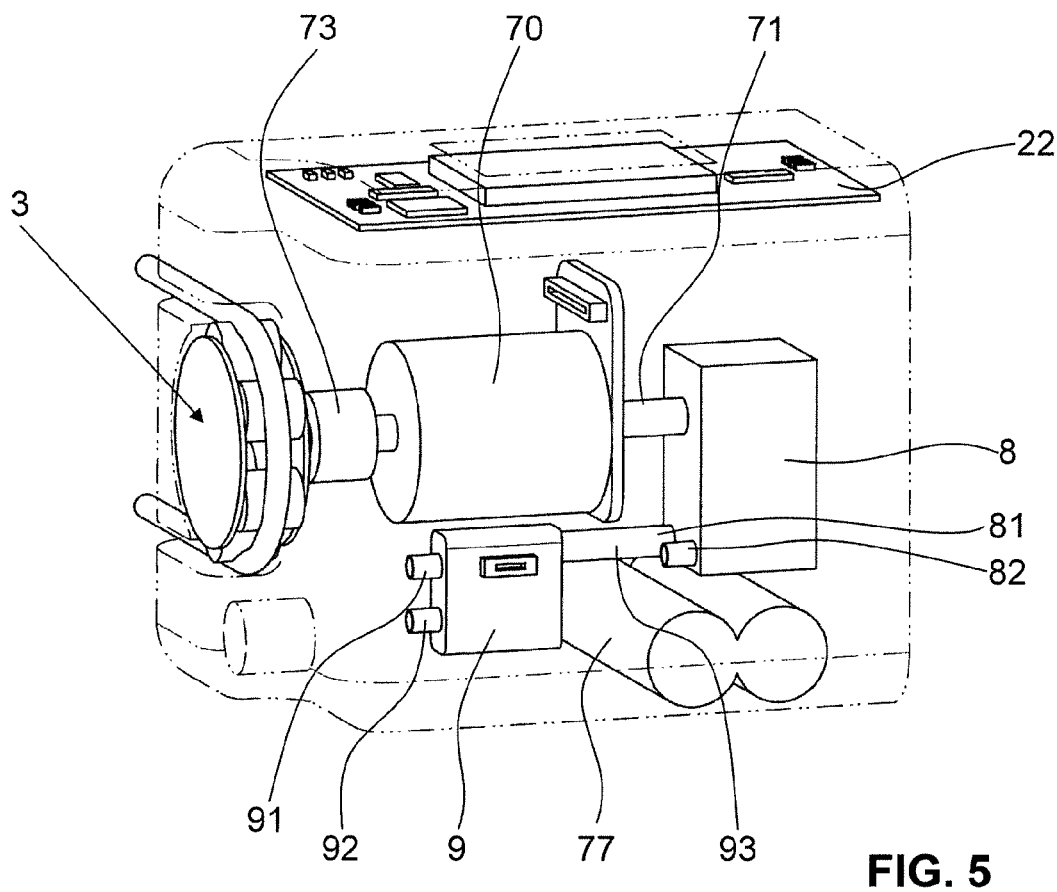
FIG. 5 shows a perspective view of a schematically shown device according to a second embodiment according to the invention, wherein the pump unit housing is indicated only with dashed lines.
Figure 6:
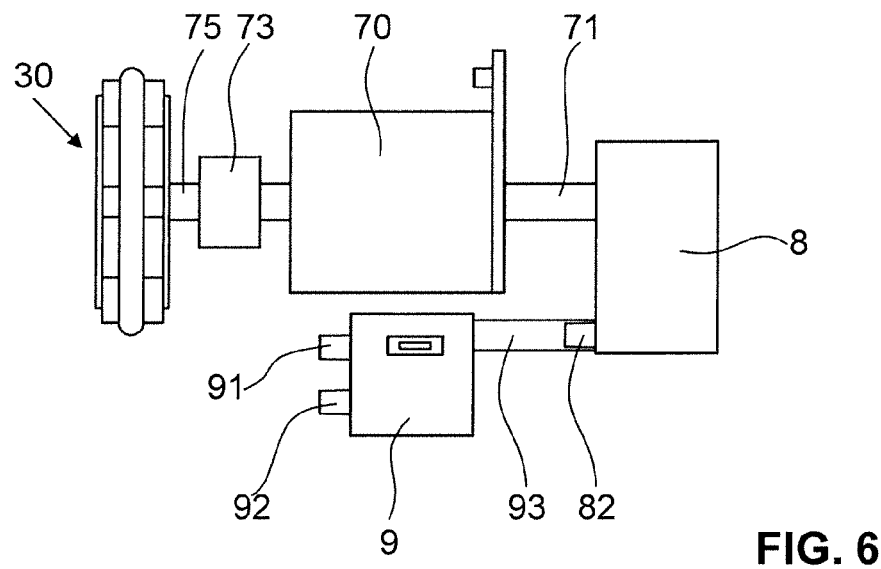
FIG. 6 shows a top view of the drive train, the pump head of the peristaltic pump, the diaphragm pump and the pneumatic valve of the device of FIG. 1.

In FIGS. 1 to 7, different embodiments of devices according to the invention are shown, wherein FIGS. 1 to 4 relate to a first embodiment, FIGS. 5 and 6 to a second embodiment and FIG. 7 to a third embodiment. FIGS. 8 and 9 show a fluid-collecting container 5', which can be connected up to the device shown in FIG. 7.

The devices shown in FIGS. 1 to 7 are suitable in particular for the combined negative pressure and instillation/irrigation treatment of wounds on the human or animal body. Accordingly, the following remarks respectively relate to the use of devices in the combined negative pressure and instillation/irrigation treatment. In principle, however, it would also be possible to use these devices, with appropriately adapted design, for catheter flushing, eye surgery, fat removal or some other medical application.

In FIGS. 1 to 9, elements having an identical or similar technical function and effect are in the various embodiments respectively provided with the same reference numerals or have the same reference numeral, but provided with a hyphen (').

Figure 1:
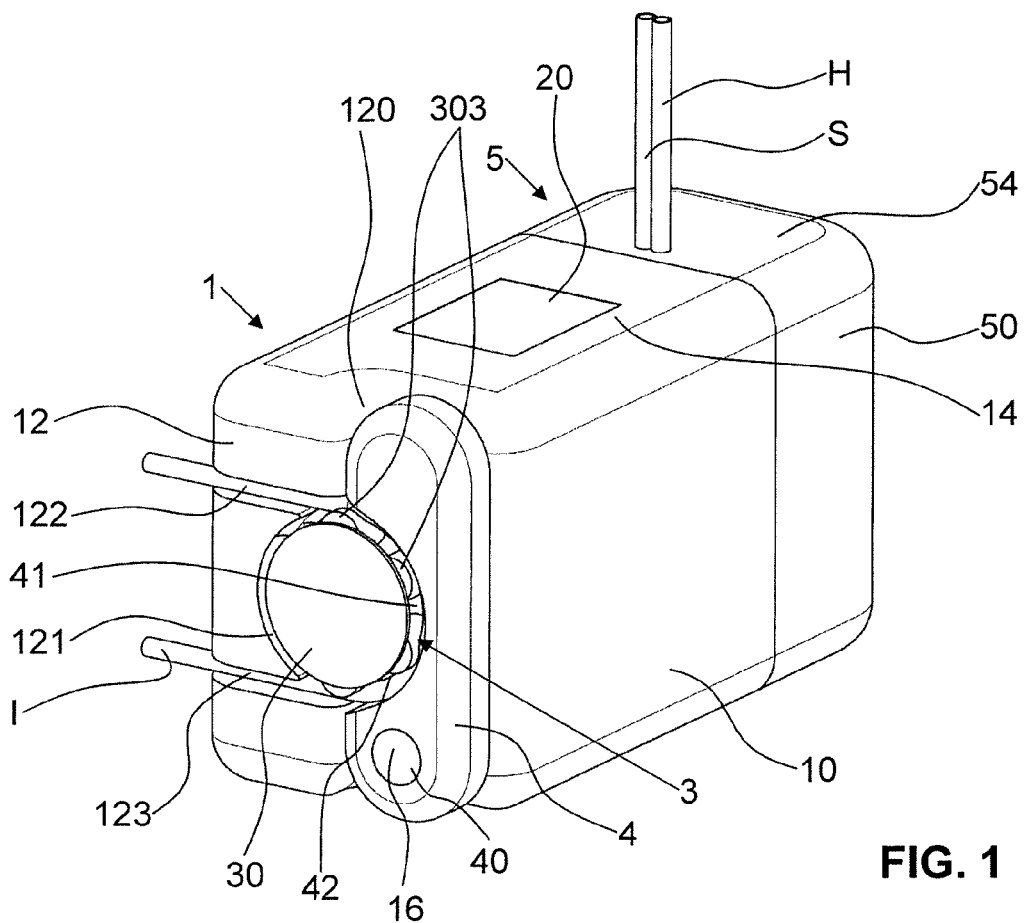
FIG. 1 shows a perspective view of a schematically shown device according to a first embodiment according to the invention.

As is clearly apparent in FIG. 1, the device of the first embodiment according to the invention of FIGS. 1 to 4 has a pump unit housing 1 with a fluid-collecting container 5 which can be connected up thereto.

Figure 2:
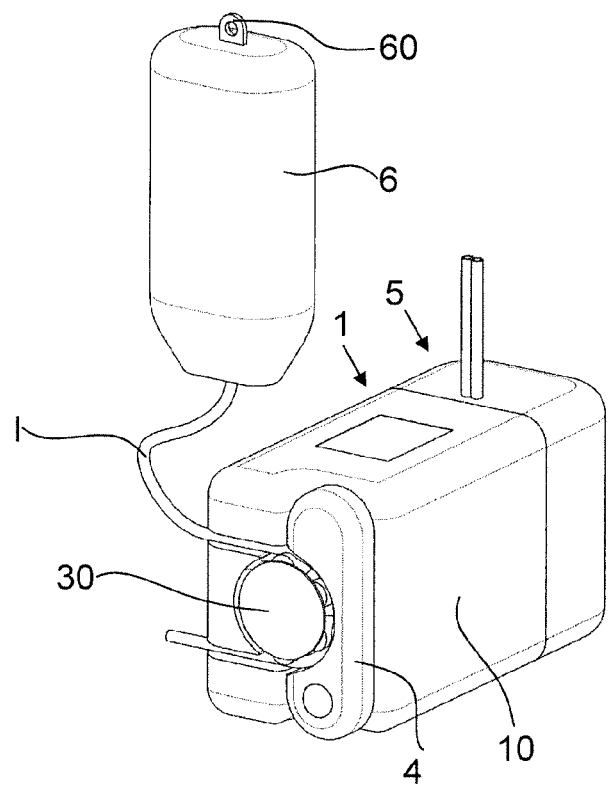
FIG. 2 shows a perspective view of the device of FIG. 1, connected to a liquid container holding instillation liquid.

The pump unit housing 1 has an overall substantially cuboid form. In FIGS. 1 and 2, a top wall 14, a front wall 10 and a side wall 12 of the pump unit housing 1 are respectively discernible. The side wall 12 has in its corner region, where it is connected to the front wall 10, an indentation 120, which extends along the entire height of the side wall 12.

The fluid-collecting container 5 likewise has an overall substantially cuboid form. In FIGS. 1 and 2 can respectively be seen a top wall 54 and a front wall 50. If the fluid-collecting container 5 is properly connected up to the pump unit housing 1, as is shown in FIGS. 1 and 2, it forms together with this same an overall substantially cuboid shape with rounded outer edges and outer corners. The external walls of the pump unit housing 1 and of the fluid-collecting container 5 are here arranged respectively in mutual alignment.

Leading through the top wall 54, out of the fluid-collecting container 5, are two tubes, of which one forms a secretion line S and the other forms an auxiliary line H. The secretion line S serves to connect the fluid-collecting container 5 to a cavity or wound of a patient, from which body fluids are due to be aspirated, wherein the aspirated body fluids are collected in the fluid-collecting container 5. By means of the auxiliary line H, it is possible, where necessary, to flush the secretion line S and/or to measure the pressure or the flow rate in the secretion line S. To this end, the auxiliary line H preferably opens out close to the cavity or wound into the secretion line S.

The secretion line S opens out with its patient-remote end into the inside of the fluid-collecting container 5. In its side wall facing the pump unit housing 1, the fluid-collecting container 5 has a vacuum port (not discernible in the figures), which connects a vacuum pump disposed in the pump unit housing 1 to the inside of the fluid-collecting container 5, so that, by means of the vacuum pump inside the fluid-collecting container 5, a vacuum can be generated. The auxiliary line H leads via the fluid-collecting container 5, and an auxiliary port (likewise not discernible in the figures) disposed in the same side wall as the vacuum port, directly into the pump unit housing 1.

The side wall 12 of the pump unit housing 1 has a centrally disposed depression 121. The depression 121 has the form of a semi-circular surface and is configured open towards the indentation 120. The depression 121 has the same depth as the indentation 120. Moreover, the side wall 12 forms a first guide channel 122 and a second guide channel 123 in the form of depressions arranged in straight lines and in parallel. The two guide channels 123 open out, at the uppermost or at the lowermost point of the semi-circular-surface-shaped depression 121, respectively tangentially into this same.

Onto a locating pin 16 provided on the lower region of the indentation 120 of the side wall 12 can be mounted a plug-on part 4, which has approximately the same dimensions as the indentation 120. For the reception of the locating pin 16, the plug-on part 4 has a cut-out 40 configured complementary thereto. The locating pin 16 can in particular be configured for engagement in the cut-out 40. Further and/or differently fastening structures for attaching the plug-on part 4 to the pump unit housing 1 are, of course, conceivable.

The plug-on part 4 has a recess 41, which is open laterally towards the depression 121 and has the form of a semi-circular surface. Together with the depression 121, the recess 41, if the plug-on part 4 is properly attached to the pump unit housing 1, forms a circular-surface-shaped depression. Within this circular-surface-shaped depression is disposed a pump head 30 of a peristaltic pump 3.

On the periphery of the circular pump head 3, a plurality of pressure rollers 303 are mounted in a freely rotatable manner at regular intervals along the peripheral direction. The semi-circular-arc-shaped space between the pump head 3 and the plug-on part 4 forms a tube bed 42. The upper end of this tube bed 42 opens out into the first guide channel 122, and the lower end into the second guide channel 123. By means of removal of the plug-on part 4 from the pump unit housing 5, a tube can be easily inserted into the guide channels 122 and 123 and the tube bed 42, or removed therefrom.

During operation of the device, the pump head 3 rotates about its longitudinal centre axis, so that the pressure rollers 303 roll on a tube inserted in the tube bed 42. This tube forms an instillation line I and, as shown in FIG. 1, is inserted in the first and the second guide channel 122, 123, as well as the tube bed 42. In the region of the tube bed 42, the instillation line I is diverted through 180°. As they roll, the pressure rollers 303 press the tube respectively against the plug-on part 4, so that a fluid substance contained in the instillation line I, owing to the mechanical deformation of the tube, is forced through this and conveyed towards the wound region. The peristaltic pump 3 is thus formed in particular by the pump head 30, the tube bed 42 and that portion of the instillation line I which is correspondingly inserted therein.

With the aid of the peristaltic pump 3, a fluid substance is supplied to the cavity or wound of the patient through the instillation line I. The substance can be, for instance, a physiological or non-physiological saline solution, a drug, or a mixture thereof. The instillation substance can serve to flush a wound or cavity. It can also, however, serve for the introduction of a medication or for the local anaesthetization of the wound region.

As is shown in FIG. 2, the instillation line I can in particular be connected to a liquid container 6 in which an instillation liquid is stored. The liquid container 6, which is here configured as a pouch, has a hanger 60, in order to suspend it for example from an infusion stand, with respect to the gravitational direction, above the peristaltic pump 3. In this way it is ensured that instillation liquid is at all times present in the region of the peristaltic pump.

In the region of the top wall 14 of the pump unit housing 1 is disposed a display and control panel 20. With the aid of the display and control panel 20, the device can be operated, and in particular the functions of the peristaltic pump 3 and of the vacuum pump housed in the pump unit housing 1 can be adjusted. Moreover, the display and control panel 20 can serve to display information on the status of the device, such as, in particular, current delivery rates and cycles, etc.

The inner workings of the pump unit housing 1 are shown schematically in FIGS. 3 and 4. Inside the pump unit housing 1 is housed, in particular, a drive train 7 having a drive in the form of a motor 70. The motor 70, which is preferably a brushless direct-current motor, serves to drive the peristaltic pump 3 and the vacuum pump, which latter is here configured as a diaphragm pump 8. By means of a fastening plate 700, the stator of the motors 70 is fastened in a rotationally secure manner to the pump unit housing 1.

The motor 70 has a rotor, which is connected in a rotationally secure manner to a motor shaft 71. On the basis of the rotational direction of the rotor of the motor 70, a rotational axis of the drive train 7 is defined. The motor shaft 71, the longitudinal centre axis of which coincides with the rotational axis, projects with its two end regions out of the motor 70 to both sides. By means of a first freewheel 72 the first end region of the motor shaft 71 is connected to a first drive shaft 74, and by means of a second freewheel 73 the second end region of the motor shaft is connected to a second drive shaft 75. The freewheels 72 and 73 constitute couplings which act only in one rotational direction, i.e. transmit the rotary motion of the motor shaft 71 to the first or second drive shaft 74, 75 only when the motor shaft 71 rotates in a specific direction. If the rotation speed of the drive shaft 74 or 75 is here, however, already greater than that of the motor shaft 71, no torque transmission takes place in the corresponding freewheel 72 or 73. The freewheels 72 and 73 can therefore also be referred to as overrunning clutches.

The first drive shaft 74 and the second drive shaft 75 extend with their respective longitudinal centre axes along the rotational axis of the drive train 7. The rotational directions in which a torque transmission from the motor shaft to the first or second drive shaft 74, 75 takes place are oriented in reverse directions for the two freewheels 72 and 73. When the motor shaft 71 is rotated in the anti-clockwise direction, only a torque transmission to the first drive shaft 74 therefore occurs, whilst the second drive shaft 75 remains idle. In this case only the diaphragm pump 8, but not the peristaltic pump 3, is driven. By contrast, when the rotational direction of the motor 70 and thus of the motor shaft 71 is reversed, only the peristaltic pump 3, but not the diaphragm pump 8, is driven.

In the present illustrative embodiment, the drive train 7 is thus formed by the motor 70, the motor shaft 71, the two freewheels 72 and 73, and by the first drive shaft 74 and the second drive shaft 75. Owing to the two freewheels 72 and 73 oriented in reverse directions, it is ensured in this embodiment that in any event only one of the two pumps 3 and 8 is in operation. Depending on the rotational direction of the motor 70, either the peristaltic pump 3 or the diaphragm pump 8 is driven.

The diaphragm pump 8 serves to generate a vacuum in the fluid-collecting container 5 in order to aspirate body fluids via the secretion line S and to collect these in the fluid-collecting container. To this end, the diaphragm pump 8 has a vacuum port 81, which, via a line (not illustrated in the figures), is connectable to the container-side vacuum port of the fluid-collecting container 5. Moreover, the diaphragm pump 8 has an outlet 82 in order to expel the aspirated air through this same. To this end, the outlet 82 is connected to a line (not shown in the figures), which opens out into the environment, i.e. outwards. The drive of the diaphragm pump 8 is realized via the first drive shaft 74.

As has already been mentioned, the peristaltic pump 3 has a plurality of pressure rollers 303. These pressure rollers 303 are mounted in a freely rotatable manner about their respective axes on a pump head 30 and are disposed between two mutually parallelly extending circular plates 301 and 302. The axes of the pressure rollers 303 here respectively connect the two plates 301 and 302 one to the other. The pump head 30 can be set by the second drive shaft 75 in rotary motion about the rotational axis of the drive train 7.

Inside the pump unit housing 1 is housed, moreover, an electronic unit 2. The electronic unit 2 has a printed circuit board (PCB) 22, on which electronic components 21, such as, in particular, a control unit, a motor end stage, pressure measuring sensors, a memory chip etc., are disposed. On the PCB 22 are further disposed a display and control elements, if need be a touch screen, in order to form the display and control panel 20. The electronic unit 2 serves in particular to adjust and regulate the rotational direction and the rotation speed of the motor 70, in dependence on the inputs made by the user at the display and control panel 20.

For the supply of electric power to the motor 70 and the electronic unit 2, an energy store in the form of an accumulator 77 is further housed inside the pump unit housing 1.

The second embodiment according to the invention, shown in FIGS. 5 and 6, is configured the same as the embodiment of FIGS. 1 to 4, apart from some few differences which are set out below.

In contrast to the embodiment of FIGS. 1 to 4, that of FIGS. 5 and 6 has only a single freewheel 73, which connects the motor shaft 71 to that drive shaft 75 which drives the pump head 30. The drive of the diaphragm pump 8 is realized directly via the motor shaft 71. It is thereby possible to drive the two pumps 3 and 8 simultaneously, so that both a secretion aspiration through the secretion line S and a supplying of instillation liquid through the instillation line I can occur at the same time. When the rotational direction of the motor 70 is reversed, because of the freewheel 73 only the diaphragm pump 8, however, is driven.

In order nevertheless to enable, in the simultaneous operation of the diaphragm pump 8 and the peristaltic pump 3, any chosen adjustment of the vacuum prevailing in the fluid-collecting container 5 and in the secretion line S, in the present embodiment, via a connecting line 93, a pneumatic valve 9 is connected up to the vacuum port 81 of the diaphragm pump 8. The pneumatic valve 9 has a vacuum port 91, which, via a line (not illustrated in the figures), is connected to the container-side vacuum port of the fluid-collecting container 5. Moreover, the pneumatic valve has an inlet 92, which, via a further line (likewise not shown), opens out into the environment.

Depending on the valve setting of the pneumatic valve 9, the whole of the suction power generated by the diaphragm pump 8, or only a part thereof, is present at the vacuum port 91. The pneumatic valve 9 can even be set such that the connecting line 93 is directly connected to the inlet 92, so that, in the fluid-collecting container 5 and thus in the secretion line S, despite the operation of the diaphragm pump 8, atmospheric pressure prevails. In such a valve setting, instillation liquid can be supplied through the instillation line I without an aspiration simultaneously taking place through the secretion line S. Preferably, the setting of the pneumatic valve 9 is regulatable by the electronic unit 2, in dependence on the inputs made by the user at the display and control panel 20.

A third embodiment according to the invention is shown in FIGS. 7 to 9. The device of this embodiment comprises a pump unit housing 1', shown in FIG. 7, to which a fluid-collecting container 5', shown in FIGS. 8 and 9, is connectable.

Here too, the pump unit housing 1' has an overall substantially cuboid form having a front wall (not shown in FIG. 7), a rear wall 11', a first side wall 12' and a second side wall 13', as well as a top wall 14' and a bottom wall 15'. The front wall and the rear wall 11' each have a wall edge, which wall edges protrude beyond the first side wall 12' arranged therebetween. The fluid-collecting container 5' is held between these wall edges and can thereby be fastened easily, but nevertheless in a secure and protected manner, to the pump unit housing 1'.

For the hanging and holding of the fluid-collecting container 5' on the pump unit housing 1', on the pump unit housing 1' are provided receiving hooks 190', in which correspondingly configured and arranged pins 554' of the fluid-collecting container 5' can engage. By means of a retaining boss 191' which is attached to a spring-loaded element and is configured for snap-locking into a detent notch 553' configured on the fluid-collecting container 5', the fluid-collecting container 5' is secured to the pump unit housing 1'. In order to release the latching connection between the retaining boss 191' and the detent notch 553', the spring-loaded element to which the retaining boss 191' is attached can be forced downward counter to the spring force.

The protruding wall edges of the front wall and the rear wall 11', as well as the receiving hooks 190' and the retaining boss 191', together form a container receptacle 19' of the fluid-collecting container 5'.

The pump unit housing 1' has a housing-side vacuum port 17', which, upon the attachment of the fluid-collecting container 5' to the pump unit housing 1', is coupled to a container-side vacuum port 551' correspondingly provided on the fluid-collecting container 5', so that, via the ports 17' and 551', a vacuum can be generated inside the fluid-collecting container 5'.

Moreover within the first side wall 12' is provided an adapter socket 18', which serves to receive a tube adapter (not shown in the figures). The tube adapter connects a secretion line (not shown in the figures), via a container-side secretion port 552' provided on the fluid-collecting container 5', to the inside of the fluid-collecting container 5'.

Inside the pump unit housing 1' is housed a drive train 7' having a motor 70' and a motor shaft 71' connected to the motor 70'. Here too, the motor 70' can be, in particular, a brushless direct-current motor.

The motor shaft 71' drives directly, with a first end region, a diaphragm pump (not shown in FIG. 7 for representational reasons). With a second end region (not visible in FIG. 7), the motor shaft 71' is connected to a freewheel 72', which connects the motor shaft 71' to a drive shaft 75'. The drive shaft 75', which extends along the rotational axis of the motor shaft 71', projects through the first side wall 12'.

On the outer side of the pump unit housing 1', a coupling element 76' is attached in a rotationally secure manner to the end of the drive shaft 75'. The coupling element 76' has the shape of a gearwheel. In the present case, it is a gearwheel having four teeth. Via the coupling element 76', a pump head 30', integrated in the fluid-collecting container 5', of a peristaltic pump 3' can be driven, if the fluid-collecting container 5' is properly attached to the pump unit housing 1'.

In principle, it is also conceivable, of course, that the pump head 30' is not integrated in a fluid-collecting container, but on any chosen other part, such as, for instance an intermediate part which can be coupled between the pump unit housing 1' and a fluid-collecting container. The pump head 30' could, in particular, also constitute a part of a container in which the instillation substance is accommodated. The container could have an identification feature and the device an identification unit, in order to identify what type of substance is contained in the container. The device could then be configured to select, in dependence on the identified type of substance, one of several possible operating modes for driving the first pump and the second pump or the coupling elements, or to limit the selection of the operating modes for the user in dependence on the substance. The identification feature can in particular be electronically readable, for example by means of RFID. Such an identification and subsequent preselection of operating modes is also conceivable, of course, when the pump head is not integrated in the container holding the substance to be identified.

The fluid-collecting container 5' has a front wall 50', a rear wall (not visible in the figures), two side walls 52' and 53', as well as a top wall 54 and a bottom wall (likewise not visible). These walls are formed by a base part 55', made of an opaque material, and a transparent part 56'. On that side wall 52' which is formed solely by the transparent part 56', a filling level scale 560' is provided.

That side wall 53' which is formed solely by the base part 55' has a centrally disposed, annular depression 555'. Within the annular depression 555', the side wall 53' forms a concentrically disposed bearing journal 556', which has an upper, upwardly open cut-out 557'.

In the annular depression 555' is accommodated a ring gear 57', which is arranged in a freely rotatable manner around the bearing journal 556'. In the ring gear 57', pressure rollers (not visible in the figures) are mounted in a freely rotatable manner at regular intervals along the peripheral direction. Upon the rotation of the ring gear 57', the pressure rollers serve to roll onto a tube inserted in the annular depression 555' on the radial outer side of the ring gear 57'. The tube can in particular form an instillation line I. By the rolling of the pressure rollers on the tube, the latter is compressed and a fluid present therein is conveyed.

On its radial inner side is configured on the ring gear 57' a circumferential toothing 570'. Assuming the fluid-collecting container 5' is properly attached to the pump unit housing 1', the toothing 570' enters into engagement with the coupling element 76', so that, upon rotation of the drive shaft 75', the rotary motion is transmitted via the coupling element 76' to the ring gear 57'.

The ring gear 57' thus forms together with the annular depression 555' and the instillation line I inserted therein a peristaltic pump 3', wherein the ring gear 57' forms the pump head 30'. In order to guide the instillation line I towards the annular depression 555' and back away from this, within the first side wall 12' are configured appropriate guide channels for receiving the instillation line I, which guide channels run in a straight line and in parallel from the annular depression 555' upwards to the top wall 54'.

Advantageously, substantially all parts of the fluid-collecting container 5', inclusive of the ring gear 57' and the pressure rollers which are attached thereto, are produced by injection moulding. Since the fluid-collecting container 5' usually constitutes a disposable part, which is often exchanged and disposed of already after a single application, the requirements placed on the therein integrated pump head 30 are relatively low. The production costs for the total device can thereby be considerably lowered in comparison to a device in which the pump head is disposed in or on the pump unit housing and hence has to be designed for a much longer working life.

In all embodiments, the drive train 7 or 7' can comprise, moreover, one or more gear mechanisms in order to change the rotation speed of the pump head 30 and/or the pumping frequency of the diaphragm pump 8 in relation to that of the motor 70. By means of the at least one gear mechanism, the peristaltic pump 3, 3' and the diaphragm pump 8, although they have a common drive in the form of the motor 70 or 70', can be operated with different or equal pumping frequencies, according to choice. The gear mechanism(s) can, but do not have to be combined with the freewheels 72, 72' and/or 73. They can thus be provided additionally or alternatively to the freewheels 72, 72' and 73.

Self-evidently, the invention which is described here is not limited to the mentioned embodiments and a large number of modifications is possible. Thus the first and the second pump, for example, do not necessarily exist in the form of a diaphragm pump and a peristaltic pump, but rather, depending on the application, any chosen pump types can in principle be used for both pumps. Preferably, the mentioned embodiments relate to devices which are respectively of portable configuration, so that they can comfortably be carried by the user alone and without excessive effort. In principle, the described devices can be dimensioned according to choice. A large number of further modifications is conceivable.

The invention claimed is:

1. A device for aspirating body fluids and for supplying a substance to a human or animal body, comprising
    a first pump in a form of a vacuum pump for an aspiration of the body fluids through a suction line;
    a second pump for conveying the substance to the human or animal body;
    a drive for driving both the first pump and the second pump;
    a pump unit housing having an interior in which at least the first pump and the drive are housed;
    a freewheel, by means of which the second pump is coupled to the drive in such a way that a rotary motion of the drive is transmitted to the second pump only when the drive rotates in a specific direction; and
    a pneumatic valve, which allows the first pump to be fully connected to an environment instead of to the suction line, in order to fully aspirate air from the environment instead of the body fluids, and which allows the first pump to be partially connected to the environment, in order to vary a suction power for the aspiration of the body fluids, whilst a drive power for driving the first pump remains constant,
    wherein the second pump is disposed on an outer side of the pump unit housing and includes a plug-on part capable of being plugged on and rotated relative to the pump unit housing, the plug-on part and the pump unit housing forming a tube bed of the second pump.

2. The device according to claim 1, wherein the second pump is a peristaltic pump.

3. The device according to claim 1, wherein the device serves for a combined negative pressure and instillation treatment of wounds on the human or animal body.

4. The device according to claim 1, wherein the device serves for a combined aspiration and flushing in a liposuction or for a combined aspiration and flushing in an eye surgery.

5. The device according to claim 1, wherein the first pump is coupled to the drive by means of a further freewheel, which has an opposite freewheel direction in comparison to the freewheel by means of which the second pump is coupled to the drive.

6. The device according to claim 1, wherein the drive is constituted by a brushless direct-current motor.

7. The device according to claim 1, comprising a drive train, in which the drive is disposed between the first pump and the second pump.

8. The device according to claim 1, wherein the device is configured such that a pumping power of the first pump, on the one hand, and a pumping power of the second pump, on the other hand, are adjustable largely independently of each other.

9. The device according to claim 1, wherein the wherein a container is attachable to the device, the container containing the substance to be supplied, and wherein the container has an identification feature and the device has an identification unit in order to identify what type of the substance is contained in the container, and wherein the device is configured to select, in dependence on the identified type of the substance, one of several possible operating modes for driving the first pump and the second pump.

10. The device according to claim 1, wherein the first pump is a diaphragm pump.

11. The device according to claim 2, wherein the pump unit housing has a side wall with a depression within which a pump head of the peristaltic pump is arranged.

12. The device according to claim 2, wherein the pump unit housing has a side wall which forms a first guide channel and a second guide channel in a form of depressions, and wherein the peristaltic pump comprises the tube bed which opens out into the first guide channel and into the second guide channel.

13. A device for aspirating body fluids and for supplying a substance to a human or animal body, comprising:
    a first pump in a form of a vacuum pump for an aspiration of the body fluids through a suction line;
    a second pump, in order to convey the substance to the human or animal body by means of the second pump;
    a drive for driving the first pump and the second pump;
    a freewheel, by means of which the second pump is coupled to the drive in such a way that a rotary motion of the drive is transmitted to the second pump only when the drive rotates in a specific direction; and
    a pneumatic valve, which allows the first pump to be fully connected to an environment instead of to the suction line, in order to fully aspirate air from the environment instead of the body fluids, and which allows the first pump to be partially connected to the environment, in order to vary a suction power for the aspiration of the body fluids, whilst a drive power for driving the first pump remains constant;

wherein the second pump is disposed on an outer side of an pump unit housing and a plug-on part and the pump unit housing form a tube bed of the second pump.

\* \* \* \* \*

UNITED STATES PATENT AND TRADEMARK OFFICE
CERTIFICATE OF CORRECTION

PATENT NO.         : 11,644,026 B2
APPLICATION NO.    : 16/333877
DATED              : May 9, 2023
INVENTOR(S)        : Hilmar Ehlert Page 1 of 1

It is certified that error appears in the above-identified patent and that said Letters Patent is hereby corrected as shown below:

In the Claims

At Column 11, Line 45, "comprising" should be -- comprising: --.

At Column 12, Line 29, "wherein the wherein" should be -- wherein --.

Signed and Sealed this
Seventh Day of November, 2023

Katherine Kelly Vidal
*Director of the United States Patent and Trademark Office*